United States Patent [19]

Becker et al.

[11] Patent Number: 4,648,876
[45] Date of Patent: Mar. 10, 1987

[54] BREATHABLE PANTY LINER

[75] Inventors: Patricia E. Becker, Manalapan Township, Monmouth County; Kenneth J. Molee, Hightstown, both of N.J.

[73] Assignee: Personal Products Company, Milltown, N.J.

[21] Appl. No.: 423,389

[22] Filed: Sep. 24, 1982

[51] Int. Cl.$^4$ .............................................. A61F 13/16
[52] U.S. Cl. .................... 604/370; 604/372; 604/374; 128/156
[58] Field of Search ............. 604/367, 370, 374, 372, 604/378; 128/156; 156/227; 2/406

[56] References Cited

U.S. PATENT DOCUMENTS

| 3,367,329 | 2/1968 | Dibelius | 128/156 |
| 3,426,754 | 2/1969 | Bierenbaum et al. | 128/156 |
| 3,486,968 | 12/1969 | Mater | 128/156 |
| 3,989,867 | 11/1976 | Sisson | 128/156 |
| 4,107,426 | 8/1978 | Gordon | 128/156 |
| 4,341,216 | 7/1982 | Obenour | 604/370 |

Primary Examiner—Robert Peshock
Assistant Examiner—John G. Weiss
Attorney, Agent, or Firm—Jason Lipow

[57] ABSTRACT

A panty liner is provided which will prevent the strike through of absorbed liquid body fluids while allowing evaporated body fluids to pass therethrough. The liner includes one or more plies of a fibrous layer which is liquid repellent and air permeable.

12 Claims, 5 Drawing Figures

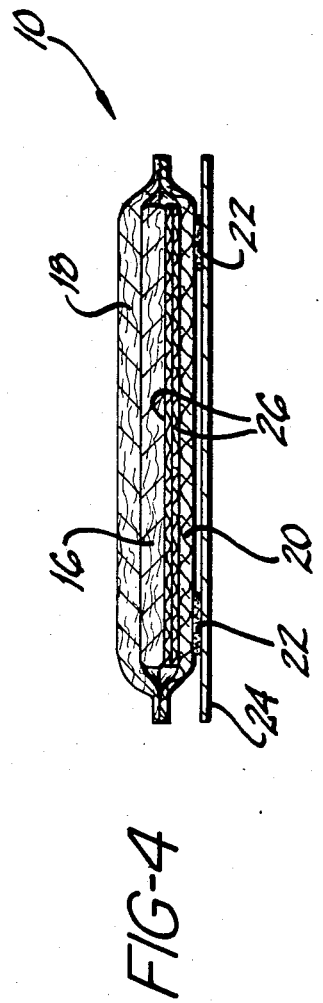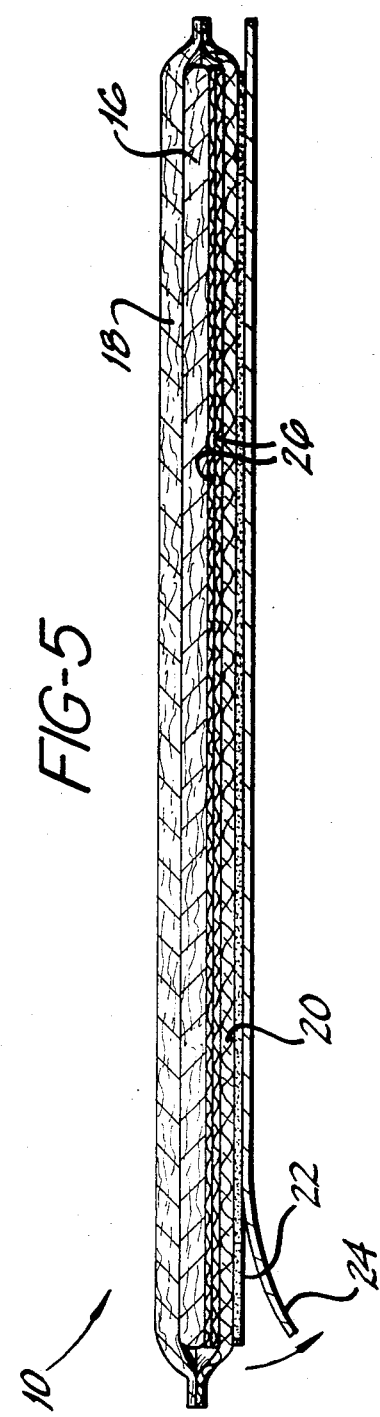

BREATHABLE PANTY LINER

BACKGROUND OF THE INVENTION

This invention relates to thin absorbent panty liners for protecting the wearer's undergarment both during intermenstrual use and, in conjunction with other catamenial devices, during menstrual use.

Several products are now on the market to provide the user with protection from the staining of undergarments, and particularly during non-menstruating days. These products generally are designed to be worn in the crotch portion of an undergarment and comprise a body facing side which is pervious to body fluids, an absorbent body which is capable of absorbing and retaining quantities of body fluid and a fluid impermeable backing on the garment facing side of the product for presenting the fluid absorbed and retained from "striking through" onto the crotch surface of the undergarment. Generally these products have been provided with a layer of pressure-sensitive adhesive for adhering the product to the crotch portion of the garment.

In the main, these intermenstrual products utilize materials of construction similar to the larger menstrual products in popular use. Accordingly, the fluid impermeable backing designed to prevent strike through comprise a totally fluid occlusive polymeric film with a film of polyethylene being the material of choice. Several drawbacks have been discovered when using such totally fluid occlusive products. In contrast to the forerunner menstrual products, the intermenstrual products of concern herein are designed to be worn every day and to be changed much less frequently than the menstrual products. Accordingly, body fluids absorbed by the products will remain carried by the wearer throughout the day and eventually, should such intermenstrual discharges be voluminous or should the wearer perspire heavily, the products will actually accumulate wetness which will add to, rather than obviate, user discomfort. The accumulation of body fluid for an entire day may even cause the product to become saturated toward the end of the day and fail, allowing body fluids to stain the undergarment and possibly embarrass the wearer. Still further, the accumulation of body fluids, particularly in aqueous solution, lends itself to the breakdown of these fluids and the proteanacous matter associated therewith into odiferous compounds which can cause embarrassment. While the odors can be masked by the use of perfumes and the like, such masking is dependent on the volatilization of the essential oils in the perfume and the fluid occlusive films used heretofore as backings for these products tend to frustrate such volatilization and inhibit the masking effect of such perfumes.

Several prior suggestions exist in the art of catamenial napkins and diapers for rendering a relatively liquid impervious polyethylene film, pervious to water vapor transmission. For example, in U.S. Pat. No. 3,989,867 issued to J. B. Sisson on Nov. 2, 1976 a polyethylene backing sheet is described having cone shaped bosses which will allow water vapor to evaporate from the surface of the absorbent material in a diaper, catamenial napkin or dressing. The actual open surface of such a backing is said to be from about ½% to about 10%. As such, it is clear that at least 90% of the backing is in fact impervious. As is recited in the above set out patent such a system is said to allow the evaporation of substantial quantities of liquid from such products as diapers where the products have relatively thick absorbing pads and the quantity of liquid deposited therein is substantial. Undoubtedly, this is because sufficient liquid is deposited to essentially wet through local areas of the absorbent and create, by wicking, a wet area at the interface between the backing and the absorbent body which is large enough to span several of the cone shaped bosses. Unfortunately, this situation does not exist for the panty liners which are the subject matter of this invention. In this latter case, the deposition is slight and the area of the pad, in contact with the backing, that is wet with liquid, is small. Thus, in the panty liners of this invention, very little wet interfacial surface would be in contact with open backing surface having what may be considered macropores and hence little evaporation occurs.

To obviate this problem, a requirement for the backing would be to increase the open area of the polymeric film and, of course, this must be done without creating large pores which will result in strike through. One such backing exists in the surgical dressing art and is described in U.S. Pat. No. 3,426,754 issued on Feb. 11, 1969 to Harvey S. Bierenbaum, et al. Described therein is a polymeric film having what is termed micropores i.e., extremely small openings. Unfortunately such a material is prohibitively expensive when employed in products such as the panty liners considered herein which are designed to be used daily and then disposed of.

Accordingly, there is a need for a product especially designed for daily intermenstrual wear.

SUMMARY OF THE INVENTION

In accordance with the teachings of this invention a panty liner is provided which will preclude the accumulation of body fluids while still protecting the undergarment from stain and hence may be worn throughout the day without the risk of failure or embarrassment associated with prior products.

The panty liner comprises a garment facing side and a body facing side and is provided with a central body fluid absorbent core. Preferably, the body fluid absorbent core is overlaid, on the body facing side with a fluid permeable cover.

In accordance with this invention, the garment facing side of the absorbent core is overlaid with one or more plies of a fibrous, vapor permeable, liquid repellent layer. This layer is specifically chosen to have the properties of greatly retarding the flow of liquids therethrough while, at the same time, allowing gaseous fluids, such as, for example water vapor and air, to pass easily therethrough. As used herein these properties are characterized as liquid repellent and breathable. It has been discovered that by a combination of the fibrous, liquid repellent, breathable layer in one or more plies overlying the garment side of a relatively thin fluid absorbent body, the resulting panty liner will be capable of precluding only liquid body fluids absorbed or retained by the absorbent body from striking through the product and staining the undergarment. At the same time, the property of breathability will allow liquid body fluids to evaporate and pass through the product and the clothing of the wearer as a vapor so that liquids are not retained for long periods of time and instead the product is relatively dry for a substantial portion of the time interval during which it is worn.

In a specific embodiment, the repellent breathable layer comprises a tissue paper or layer of nonwoven fibers which has been treated with a liquid repellent agent to give it the desired repellency yet preserve its breathability.

Preferably, the repellent layer has a degree of repellency (i.e., the ability to resist liquid flowing through the layer) sufficient to support at least a 3.0 cm. column of water as measured by the Flow-Through Resistance Test set out hereinafter and each ply has an air permeability of at least 20 ft$^3$/ft$^2$/min as measured by the Frazier Air Permeometer hereafter described. Further still, the layer should be used in conjunction with other materials such that the complete product as it is configured in use, has an air permeability of at least 10 ft$^3$/ft$^2$/min and preferably at least 15 ft$^3$/ft$^2$/min. Preferably, the layer has pores which exhibit a median pore radius of less than 35 microns and still more preferably a median range from about 5 to about 30 microns. As used herein, median pore size is determined by use of mercury porosimetry measurements as herein described.

It has been discovered that by use of the repellent, breathable layers having the properties prescribed above, the product is capable of allowing even the small quantities of liquid which may be absorbed during intermenstrual use, to rapidly evaporate notwithstanding the fact that these quantities are insufficient to saturate the absorbent core of the product or even wick across the interface between the absorbent core and the repellent breathable layers. At the same time, should an unusually large discharge occur, it has been discovered that the product is capable of resisting strike through even though moderate pressures are applied such as those likely to be encountered from the wearer's movements.

In a specific embodiment of the invention, the product is provided with a scent or perfume to mask body fluid odors and this feature, in combination with the overall breathability of the product will allow the volatile oils to vaporize and perform their masking function.

BRIEF DESCRIPTION OF THE DRAWINGS

The invention will be best understood by consideration of the following description taken together with the attached drawings in which:

FIG. 4 is a transverse cross-sectional view of the panty liner of FIG. 2, taken through line 4—4; and FIG. 5 is a longitudinal, cross-sectional view of the panty liner of FIG. 2, taken through line 5—5.

DETAILED DESCRIPTION OF THE INVENTION

Figure 1:
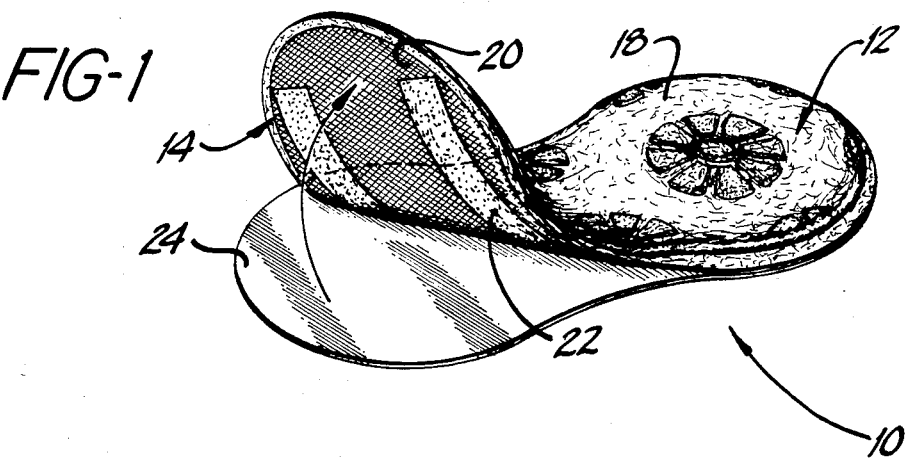
FIG. 1 is a perspective view of the panty liner of this invention with the adhesive protecting release layer being partially removed for clarity.
Figure 2:
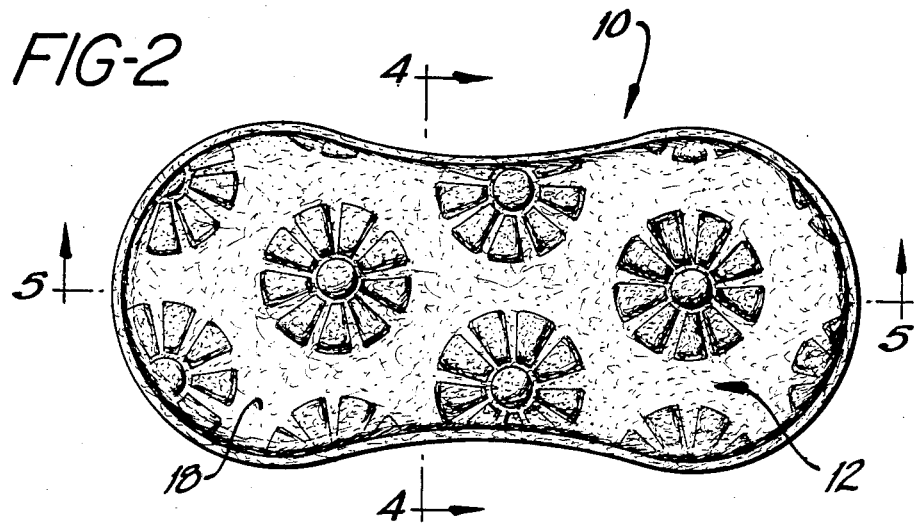
FIG. 2 is a plan view of the body facing side of the panty liner of FIG. 1.

FIGS. 1-5 illustrate, in perspective, plan and crossectional views, a panty liner 10 incorporating the teachings of this invention. As best viewed in FIGS. 2 and 3, respectively, the panty liner comprises a body facing side 12 and a garment facing side 14. The body facing side of the liner consists of one or more plies of absorbent material 16 and may also include an outer cover 18 which may or may not be capable of absorbing and retaining body fluids but, in any event, is permeable by such body fluids. The outer most surface of the body facing side of the liner 10 is provided with an aesthetically pleasing pattern of depressed areas which penetrates into the cover 18 and may also penetrate into one or more of the absorbent material plies 16.

The choice of materials for the absorbent body facing side of the liner may vary widely and may include, for example, woven or nonwoven fabrics or batts of absorbent materials such as comminuted wood pulp, rayon, cotton or other cellulosics including, for example, cellulosic materials which have been modified by chemical treatment or otherwise to improve their absorbent characteristics. Other absorbent materials such as synthetic polymers in the form of fibers, or even flexible foams may be employed.

A particularly useful material is that recited in U.S. Pat. No. 3,663,238 issued on May 16, 1972 to G. J. Liloia, et al. Described therein is a soft, lofty nonwoven comprising a mixture of approximately 25%, by weight, of relatively long (about 2.9 cm.) rayon fibers and about 75%, by weight, of short (about 0.2 cm.) wood pulp fibers and being stabilized by through bonding with a water dispersible binder present in an amount of between about 1% and about 30% of the weight of the fibers, on a dry basis. The binders of choice are the self-curing acrylic latex type, the urethane type or other similar binders.

Another particularly suitable absorbent material is a low density, highly absorbent, thermal bonded fabric comprising a mixture of absorbent fibers and staple length polyester/polyethylene conjugate fibers. The absorbent fibers are preferably wood pulp or other cellulosics which may have been treated to enhance absorbency. The conjugate fibers are fibers which comprise a polyester core surrounded by a sheath of polyethylene.

Preferably, the conjugate fibers employ high density polyethylene, that is, linear polyethylene that has a density of at least 0.94 and a Melt Index (as determined by ASTMD1238E method, employing the parameters of 190° C. and 2160 gms) of greater than 1, preferably greater than about 10, and more preferably from about 20 to about 50. The fibers may comprise from about 40 to 60 percent, by weight polyester and, preferably, from 45 to 55 percent by weight polyester, with the remainder being polyethylene. Such fibers may be used in deniers of from 1 to about 6 and may be from about ½ inch (1.27 cm.) to about 3 to 4 inches (7.62 to 10.16 cms.) long. Preferably the fabric comprises outer layers of heat fusible fibers having the mixture of wood pulp and conjugate fibers sandwiched therebetween. Such outer layers may consist of the conjugate fibers or may in fact be any heat-fusible material such as polypropylene fibers, for example. The fabric is stabilized by applying heat thereto under essentially zero pressure whereby thermal bonding takes place without destroying the integrity of the fibers and a low density for the fabric is maintained. Typically, the bulk density of such fabrics is less than about 0.15 grams per cubic centimeter.

The outer cover 18 may be any of the typical fluid pervious materials used as covers for sanitary napkins such as a woven material e.g., gauze or, for example a nonwoven material such as the ones described in U.S. Pat. No. 3,554,788 issued on Jan. 12, 1971 to M. R. Fechillas, which has the added advantage of being flushable i.e., may be disposed of by dispensing and flushing away in a water closet. The outer layer may also comprise the same material as that used as the one or more plies of absorbent material 16, provided of course, that such absorbent material has sufficient integrity in use to function as a cover for the panty liner of this invention. The aforementioned thermal bonded, conjugate fiber fabric is suitable for this purpose.

In a preferred embodiment, the outer cover 18 contains sufficient quantities of a heat sealable component, e.g., polypropylene or polyethylene, so that the cover 18 may be sealed to a backing 20 to fully enclose the product 10. In this connection, the backing 20 may be any heat sealable, relatively open fabric and has the primary function of cooperating with the outer cover 18 to contain the remaining elements of the liner. One particularly useful backing material comprises two layers; the first consisting of polyester and the other consisting of the conjugate fibers described in connection with the absorbent material 16. The fabric may be manufactured by depositing a layer of polyester fibers onto a moving screen and laying the conjugate fibers thereover. The fabric may get its integrity by entangling these fibers utilizing a process similar to that described in U.S. Pat. No. 3,485,706 issued on Dec. 23, 1969 to F. J. Evans. This process lends itself to producing a fabric having a regular pattern of apertures therethrough which is particularly suitable for use as a backing material in the breathable panty liner of this invention.

It will be understood that while it is preferred that the outer cover 18 and the backing contain heat sealable material and be sealed together by heat sealing, such is not essential. For example, the backing and cover may comprise merely cellulosic fibers and may be sealed together by use of adhesives, crimping or combinations thereof.

Figure 3:
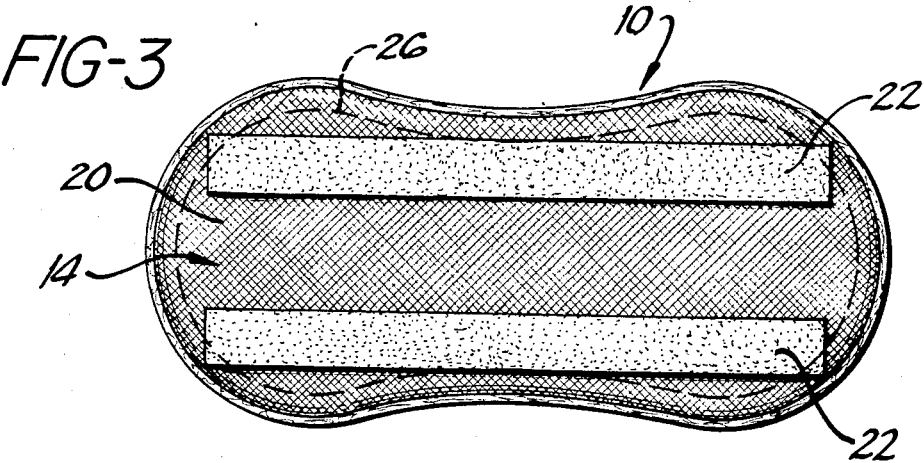
FIG. 3 is a plan view of the garment facing side of the panty liner of FIG. 1.

Overlying one or more areas on the outer surface of the backing layer 20 are adhesive layers 22 comprising pressure-sensitive adhesive for adhering the panty liner to the crotch portion of the wearer's undergarment. As best illustrated in FIG. 3, such areas comprise two longitudinally extending bands of pressure-sensitive adhesive although it will be understood by those skilled in the art that many variations in the number and shape of these adhesive areas are possible. The pressure-sensitive adhesive may be any of the already known compositions suitable for this purpose including, for example, the water based pressure-sensitive adhesives such as the acrylate adhesives e.g., vinyl acetate-2 ethyl hexyl acrylate copolymer which is generally combined with tackifiers such as, for example, ethylene amine. Alternatively, the adhesive may comprise the rapid setting thermoplastic (hot melt) adhesives such as block copolymers exemplified by styrene and butadiene/styrene copolymers. The adhesive area may also comprise a two-sided adhesive element.

As is best illustrated in FIGS. 1, 4 and 5, the adhesive areas 22 are protected by a release strip 24 to avoid undesired adhesion prior to use. The release strip 24 may be made of any suitable sheet-like material which adheres with sufficient tenacity to the adhesive areas 22 to remain in place, but which can be readily removed when the panty liner 10 is to be used. A particularly useful material is a semi-bleached kraft paper, the adhesive contacting side of which has been silicone coated to provide for easy removal from the adhesive just prior to use.

In accordance with the teachings of this invention, sandwiched between the absorbent core 16 and the backing layer 20, are one or more plies of a fibrous, repellent, breathable layer 26. This layer 26 has the properties of greatly retarding the passage of liquid therethrough while allowing gaseous fluid therethrough. Preferably each layer has a degree of repellency of at least about 3 cm. of water as measured by the Flow-Through Resistance Test hereinafter described and, still more preferably has a repellency of at least about 3.5 cm. of water. This liquid repellency notwithstanding, the layer should offer little resistance to the passage of gaseous fluids therethrough and preferably has an air permeability of at least about 20 $ft^3/ft^2/in$ as measured by the Frazier Air Permeometer test set out hereinafter.

Surprisingly, it has been discovered that when the above set out criteria are met, liquid strike through is prevented while at the same time, the rate of evaporation of liquids absorbed from the liners of this invention is essentially as great as though no barrier to liquid strike through were present. While this phenomenon is not clearly understood, it is believed to be a result of the use of a fibrous material as the layer provided to prevent strike through. This is in contrast to an occlusive film or a film which is occlusive but has been provided with perforations. In this latter case, the perforations in the film provide the flow channels for evaporating liquids while at the same time offer an adverse opportunity for liquid strike through. Accordingly, in attempting to use a perforated film, a balance must be struck: the flow area of the perforations must be limited to that which is insufficient to allow strike through and hence will concomitantly limit the flow rate of evaporated liquids.

In contrast to a perforated film, the fibrous layer of this invention does not provide channels directly connecting major surfaces of the layer. Instead, the intestices or pores defined by the fibrous nework create a tortuous path for the flow of fluids from one major surface of the layer to the other. Such path is constricted and nonlinear and hence offers substantial resistance to fluid flow. In particular, when the fibers have been chosen or treated to be hydrophobic, i.e., repellent, the flow of liquid through the constructions is believed to be governed by the resistance related to the surface tension of the liquid. If this is indeed the case, it explains the phenomenon described herein, to wit; liquid flow is greatly inhibited whereas vapor flow, not being substantially resisted by surface tension, is not inhibited to the same degree. A measure of this characteristic of the layer to resist liquid flow by virtue of surface tension resistance is the result obtained when subjectng the layer to mercury porosimetry analysis. This analysis is described in detail in Introduction to Powder Surface Area, S. Lowell, published by John Wiley & Sons, N.Y., 1979 and has been carried out by use of a device called a Quantachrome Scanning Microporosimeter, made by the Quantachrome Corp. of Syosset, N.Y. Basically, this device determines the volume of mercury forced into the pores of a sample as a function of the pressure required to fill the pores. For a given liquid, e.g., mercury, the pressure is assumed to be inversely proportional to the radius of a pore. The results of the analysis is a mean radius, i.e., the radius of the pores which are filled when one half of the total void volume of the sample is occupied with fluid. It has been found that for the purposes of this invention the layer should exhibit a mean pore radius of less than 35 microns and preferably should range from about 5 to about 30 microns.

A particularly suitable material for use as one or more of the layers 26 is a tissue paper which is treated by applying thereto a chemical agent which gives the tissue the required repellency. Preferably, each ply of the untreated tissue which comprise cellulose fibers held in place by hydrogen bonding has a base weight which may vary from about 0.2 to about 1.0 oz/yd$^2$ and still more preferably from about 0.5 to about 0.75. The tissue should also have the requisite strength to maintain its integrity during the manufacture of the product.

The tissue should be treated with sufficient repellent treating agent to meet the criteria set out above. Several such repellent treating agents are available including for example, rosens; certain resins such as shellac, East India resins, Danner resins, sien, silicone resins, the condensation products of formaldehyde with phenols, urea and melamine; emulsion of urea; insoluble fatty acids (e.g., behenic acid); acetylating agents, e.g., acetic anhydride in an inert solvent; cyanoethylating agents; or diketenes (see for example U.S. Pat. 2,627,477) or polyketenes or copolymers of polyketenes. A particularly useful treatment is achieved by use of a repellent material obtained from the Hercules, Inc. of Wilmington, Delaware and sold by them under the name, "Aquapel". This repellent comprises a mixture of alkyl ketene dimers having from 16 to 18 carbon atoms. The treatment may be carried out by passing the tissue through an aqueous bath containing the repellent. Additives may also be provided in the bath for the purposes of facilitating the process, stabilizing the active compounds or for coloring the repellent tissue for aesthetic purposes if so desired. Such additives may include for example, pH stabilizers, antifoaming agents, pigments and color stabilizers or the like.

Another useful material for employment as the liquid repellent, breathable layer of the invention is a web comprised of synthetic polymeric fibers, held together by virtue of being fusion bonded. Such a web may be made by heating an entangled mass of such fibers so as to melt them at the contacting points between adjacent fibers. Alternatively, the web may be formed at the time the fibers are extruded, by randomly forming the web while the fibers are still at least partially plastic. Examples of processes for manufacturing such webs are described in U.S. Pat. Nos. 3,595,245; 3,704,198; and 3,825,380. The fibers chosen should be thermoplastic synthetic polymers which are hydrophobic or which can be treated to be hydrophobic with polyethylene, polypropylene and polyester fibers being the materials of choice.

Irrespective of the materials of construction for the cover 18, absorbent core 16, the repellent, breathable material or the backing, these materials should be chosen and the numbers of layers selected such that the resulting product has an overall air permeability of at least 10 ft$^3$/ft$^2$/min and preferably at least 15 ft$^3$/ft$^2$/min. To accomplish this it is generally necessary that the overall thickness of the product does not exceed 1.0 cms. and preferably does not exceed 0.75 cms.

The invention will be better understood by consideration of the following examples.

EXAMPLE 1

A panty liner is prepared having the general configuration and shape illustrated in FIGS. 1-5. The product has a length of 5.00 inches (12.7 cms), a maximum width of 2.25 inches (5.72 cm.), a minimum width of 1.9 inches (4.83 cm.) and a maximum thickness of 0.21 inches (0.533 cm.). The product has an overall weight of 2.41 gms. The body facing side of the liner is provided with an outer cover constructed of a thermal bonded absorbent fabric comprising, overall, 54% by weight of wood pulp fibers and 46% by weight of conjugate fibers having a polyester core and a high density polyethylene sheath. The conjugate fibers have a staple length of 3.81 cms. and a denier of 3.0. The materials are so distributed as to provide a pulp/conjugate fiber mixture sandwiched between two veneers of conjugate fibers, the veneers having basis weights of 0.27 oz./yd$^2$. and 0.37 oz./yd$^2$., the heavier veneer ultimately being employed on the body facing side of the product. The fabric is stabilized by passing hot air through the fibers and thereby melting the high density polyethylene which bonds the fibers together upon cooling. The overall fabric has a basis weight of 3.0 oz./yd$^2$.

The absorbent core of the liner is constructed of another ply of the same material as is employed as the cover.

Two plies of repellent tissue are utilized as the repellant, breathable layers of this invention. The repellent tissue is made from untreated creped tissue having a basis weight 0.63 oz/yd$^2$/ply and has been treated in an aqueous bath incorporating the above-described Aquapel repellent. Also incorporated in the bath are diarylide yellow pigment and phthalocyamine blue pigment along with the color stabilizer ethylene-vinyl acetate latex to give the tissue a blue coloration. The water bath includes, additionally, ammonia as the pH stabilizer and a defoaming agent obtained for the Troy Chemical Company and sold by them as Troykyd 666.

The dried treated tissue is tested for repellency using the Flow Through Resistance Testing Apparatus developed by the Textile Research Institute of Princeton, N.J. and described in detail in the following articles: Miller, B and Clark, D. B., "Liquid Transport Through Fabrics; Wetting and Steady State Flow Part I. A New Experimented Approach". Textile Res. J., 48, p. 150 (1978) and Miller, B and Clark, D. B. "Liquid Transport through Fabrics; Wetting and Steady State Flow, Part II. Fabric Wetting". Textile Res. J., 48, p. 256 (1978). Briefly, the apparatus operates by moving liquid at a constant rate into contact and through a fabric while changes in pressure during contact are measured by a pressure transducer. The test allows for the determination of the head of liquid that the fabric can support before the liquid travels through the sample and appears on the surface of the fabric.

One ply of the repellent tissues has a repellency of 3.96 cm. of water and two plies exhibit a repellency of 6.04 cm. of water.

The tissue is also tested for air permeability utilizing the following Air Permeability Test. This test utilizes a Frazier Air Permeometer obtained from Frazier Precision instrument Co., of Gaithersbury, MD. Essentially the test is designed to measure the air flow rate (unit volume of air per unit flow area per unit time) through the sample under a pressure differential driving force of ½ inch of water. The sample is conditioned at 70° F. and 65% relative humidity and the test is run at these conditions. One ply of the repellent tissue exhibits an air permeability of 42.58 ft$^3$/ft$^2$/min and two plies of the repellent tissue employed exhibit an air permeability of 20.40 cm. ft/ft$^2$/min.

The tissue is also tested for median pore size utilizing the Quantachrome Scanning Macro porosimeter described above. The median pore radius is 28 microns.

The product utilizes, as a backing, the apertured, entangled fabric described above. The product is sealed about its periphery by heat sealing the outer cover to the backing.

The overall product, incorporating two plies of the repellent tissue, is tested for air permeability utilizing the above described Frazier Air Permeometer. The product exhibits an air permeability of 16.8 ft$^3$/ft$^2$/min.

EXAMPLE 2

A second panty liner is prepared, identical to that of Example 1 with the exception that in place of the two ply repellent tissue, a single ply of a web comprising polypropylene fibers is substituted as the repellent, breathable layer. This web is made in accordance with the processes described in U.S. Pat. Nos. 3,595,245; 3,704,198 and 3,825,380. The web is obtained from the Riegel Division of James River Corporation of Milford, New Jersey and has a basis weight of 0.59 oz/yd$_2$, a thickness of 0.0079 inches, a tensile strength of 1.32 lbs./in./ply., and an elongation to break of 45.6%. Because this web is heat-fusible, all components of the product are coextensive in area and all are heat-sealed together about the periphery of the liner to give added stability to the product and to facilitate processing.

The web exhibits a Flow-Through Resistance of 11.83 cm. of water and an air permeability of 183.5 ft$^3$/ft$^2$/min. The mean pore size of the web is 9.1 microns. The panty liner incorporating this web has an air permeability of 64.4 ft$^3$/ft$^2$/min.

EXAMPLE 3

A series of simulated panty liners are constructed to measure the rate at which evaporated liquid can pass through the garment facing surface of the liner. The simulated liners comprise 4 inches by 4 inches area of a liner constructed of the various materials set out in Example 1 with the exception that various materials are utilized as the repellent, breathable layer. In a first simulated liner, the repellent breathable layer is the two plies of tissue described in Example 1. In a second simulated liner the layer is a single ply of said tissue. In a third simulated liner, the layer is one ply of the Riegel polypropylene fiber web set out in Example 2 and in a fourth simulated liner no layer is provided.

A 2.5 inch by 2.5 inch pulp pad weighing 0.2 grams is saturated with 3 grams of a simulated incontinence fluid which comprise:

| Ingredient | Parts by Weight |
|---|---|
| Deionized Water | 3600.0 |
| Urea | 90.0 |
| NaCl | 30.9 |
| KCl | 11.4 |
| Red dye | 2.7 |

The saturated pad is placed in the center of the body facing side of each 4 inch by 4 inch simulated liner and the entire exposed body facing surface and peripheral edges of the sample, as well as a portion of the garment facing side of the sample are occluded with a double faced tape leaving exposed only an area on the garment facing side measuring 2 inches by 2 inches. The sample is then placed on a tray with the exposed area facing upwardly, and the tray is placed in an environment controlled at a temperature of 70° F. and a relative humidity of 65%. The system is weighed initially and then every hour for six hours and finally after 22 hours.

The percent evaporation moisture loss is calculated as:

$$\frac{(\text{original weight} - \text{weight after time interval})}{3 \text{ grams}} \times 100$$

The results are reported in Table 1 below

TABLE 1

| | Sample: Percent Moisture Loss | | | |
|---|---|---|---|---|
| Time Interval (HRS.) | 2 Ply Tissue | 1 Ply Tissue | Polypropylene Web | No Web |
| 1 | 3.54 | 3.11 | 3.80 | 3.14 |
| 2 | 7.63 | 8.12 | 9.25 | 7.55 |
| 3 | 13.93 | 14.55 | 15.41 | 13.76 |
| 4 | 18.19 | 19.65 | 20.60 | 18.77 |
| 5 | 23.27 | 25.04 | 25.96 | 24.21 |
| 6 | 28.59 | 30.90 | 31.07 | 30.44 |
| 22 | 83.62 | 84.41 | 85.48 | 83.80 |

As can be seen from the above, by incorporating the fibrous layers of this invention as the barrier to liquid strike through there is essentially no inhibition of evaporated moisture loss from the product.

We claim:

1. A panty liner to be worn in the crotch portion of an undergarment comprising:
    a central body fluid absorbent core having a body facing side and a garment facing side;
    said garment facing side being overlaid by at least one ply of a fibrous, vapor permeable, liquid repellent layer for protecting said undergarment from body fluids while allowing evaporated, body fluids to pass therethrough;
    said ply having a degree of repellency of at least 3.0 cm of water and an air permeability of at least 20 ft.$^3$/ft.$^2$/min; and
    said panty liner having an air permeability of at least 10 ft.$^3$/ft.$^2$/min.

2. The panty liner of claim 1 wherein said ply has a repellency of at least about 3.5 cm. of water.

3. The panty liner of claim 1 wherein said panty liner has an air permeability of at least 15 ft.$^3$/ft.$^2$/min.

4. The panty liner of claim 1 wherein said ply has a median pore radius of less than 35 microns.

5. The panty liner of claim 4 wherein said ply has a median pore radius ranging from about 5 to about 30 microns.

6. The panty liner of claim 1 wherein said ply comprises cellulosic fibers treated to be body liquid repellent.

7. The panty liner of claim 6 wherein said ply comprising cellulosic fibers is tissue paper.

8. The panty liner of claim 7 wherein said tissue paper has a base weight of from about 0.2 to about 1.0 oz/yd$^2$.

9. The panty liner of claim 1 wherein said ply comprises a web of synthetic polymeric fibers held together by fusion bonding.

10. The panty liner of claim 9 wherein said fibers are chosen from the group consisting of polyethylene, polypropylene, polyester fibers or mixtures thereof.

11. The panty liner of claim 10 wherein said liner has an overall thickness of less than 1.0 cm.

12. The panty liner of claim 11 wherein said liner has an overall thickness of less than 0.75 cms.

* * * * *